US006994699B2

(12) United States Patent
Houwaert et al.

(10) Patent No.: US 6,994,699 B2
(45) Date of Patent: Feb. 7, 2006

(54) PORT, A CONTAINER AND A METHOD FOR ACCESSING A PORT

(75) Inventors: Vincent Houwaert, Mont Saint-Aubert (BE); Denis Motta, Sondato (IT); Patrick Balteau, Bothey (BE); Francesco Peluso, Everlee (BE); Silvano Sforacchi, Grosotto (IT)

(73) Assignees: Baxter International Inc., Deerfield, IL (US); Baxter Healthcare S.A., Zurich (CH)

( * ) Notice: Subject to any disclaimer, the term of this patent is extended or adjusted under 35 U.S.C. 154(b) by 39 days.

(21) Appl. No.: 10/167,795

(22) Filed: Jun. 12, 2002

(65) Prior Publication Data

US 2003/0233083 A1 Dec. 18, 2003

(51) Int. Cl.

| | |
|---|---|
| ***A61B 19/00*** | (2006.01) |
| ***A61M 37/00*** | (2006.01) |
| ***A65D 33/16*** | (2006.01) |
| ***B65D 51/16*** | (2006.01) |
| ***B65D 41/32*** | (2006.01) |

(52) U.S. Cl. ...................... 604/408; 604/415; 604/403; 604/6.15; 604/905; 128/DIG. 28; 383/42; 383/60; 383/66; 383/906; 220/203.13; 220/266; 220/661; 220/541.6; 220/546; 220/562

(58) Field of Classification Search ................ 604/403, 604/415–416, 905, 4.01, 6.15, 407–411, 500, 604/518, 520, 522, 19, 82, 83, 906, 86–90, 604/200–206, 93.01, 257, 261–262, 288.01; 220/257.1, 257.2, 258.2, 258.5, 265; 128/DIG. 24; 383/904, 906; 600/573, 580, 576–579; 222/541.3, 222/541.4, 541.6, 544–546, 562–563

See application file for complete search history.

(56) References Cited

U.S. PATENT DOCUMENTS

| | | | | |
|---|---|---|---|---|
| 3,030,955 | A * | 4/1962 | Gossett et al. | 604/404 |
| 3,900,028 | A * | 8/1975 | McPhee | 604/415 |
| 3,915,212 | A | 10/1975 | Bujan et al. | 150/8 |
| 3,994,412 | A | 11/1976 | DiFiglio | 220/266 |
| 4,187,893 | A * | 2/1980 | Bujan | 604/408 |
| 4,303,067 | A | 12/1981 | Connolly et al. | 604/408 |

(Continued)

FOREIGN PATENT DOCUMENTS

DE 43 27 845 A1 3/1995

(Continued)

OTHER PUBLICATIONS

International Search Report for International Application No. PCT/US03/16835 that issued on Sep. 9, 2003.

*Primary Examiner*—Patricia Bianco
(74) *Attorney, Agent, or Firm*—Ira D. Finkelstein; Paula Kelly; Robert Barrett

(57) ABSTRACT

A port, a container and a method for accessing a port for injecting or withdrawing a liquid from the container are provided. The port may allow for the administration of, for example, a drug, to a patient and may be located on the container. The port has a septum having a target area. The port also has a support ring in contact with the septum. A cap is provided to protect the septum. The cap has a ring handle and allows for removal and exposure of the target area of the septum. A needle, for example, may be used to penetrate the septum allowing the addition or withdrawal of a liquid or other drug to or from the container.

18 Claims, 2 Drawing Sheets

U.S. PATENT DOCUMENTS

| | | | | | |
|---|---|---|---|---|---|
| 4,307,766 | A | * | 12/1981 | Tanokura | 604/408 |
| 4,464,178 | A | * | 8/1984 | Dalton | 604/174 |
| 4,479,989 | A | * | 10/1984 | Mahal | 428/35.5 |
| 4,484,916 | A | * | 11/1984 | McPhee | 604/256 |
| 4,592,092 | A | * | 5/1986 | McPhee | 383/80 |
| 4,632,673 | A | | 12/1986 | Tiitola et al. | 604/415 |
| 4,636,204 | A | * | 1/1987 | Christopherson et al. | 604/535 |
| 4,675,019 | A | * | 6/1987 | Bellhouse et al. | 604/408 |
| 4,757,911 | A | | 7/1988 | Larkin et al. | 220/265 |
| 4,911,708 | A | * | 3/1990 | Maezaki et al. | 604/408 |
| 4,985,033 | A | * | 1/1991 | Boebel et al. | 606/148 |
| 5,061,263 | A | * | 10/1991 | Yamazaki et al. | 64/403 |
| 5,104,379 | A | * | 4/1992 | Nakamura et al. | 604/111 |
| 5,137,529 | A | | 8/1992 | Watson et al. | 604/891.1 |
| 5,178,607 | A | * | 1/1993 | Lynn et al. | 604/86 |
| 5,211,634 | A | * | 5/1993 | Vaillancourt | 604/167.02 |
| 5,211,638 | A | * | 5/1993 | Dudar et al. | 604/539 |
| 5,303,838 | A | * | 4/1994 | Luch et al. | 220/270 |
| 5,342,316 | A | * | 8/1994 | Wallace | 604/167.02 |
| 5,395,365 | A | | 3/1995 | Weiler et al. | 604/415 |
| 5,405,333 | A | * | 4/1995 | Richmond | 604/257 |
| 5,425,528 | A | * | 6/1995 | Rains et al. | 251/149.1 |
| 5,433,716 | A | * | 7/1995 | Leopardi et al. | 604/415 |
| 5,490,848 | A | | 2/1996 | Finley et al. | 604/403 |
| 5,540,674 | A | | 7/1996 | Karas et al. | 604/415 |
| 5,611,792 | A | * | 3/1997 | Gustafsson | 604/403 |
| 5,611,972 | A | | 3/1997 | Gustafsson | 604/403 |
| 5,637,107 | A | | 6/1997 | Vaillancourt | 604/403 |
| 5,685,845 | A | * | 11/1997 | Grimard | 604/82 |
| 5,718,682 | A | | 2/1998 | Tucker | 604/288.02 |
| 6,090,282 | A | * | 7/2000 | Roman | 210/238 |
| 6,113,583 | A | * | 9/2000 | Fowles et al. | 604/403 |
| 6,129,228 | A | * | 10/2000 | Adams et al. | 215/45 |
| 6,200,300 | B1 | * | 3/2001 | Petriekis et al. | 604/408 |
| 6,234,335 | B1 | | 5/2001 | Gee et al. | 215/247 |
| 6,287,293 | B1 | | 9/2001 | Jones et al. | 604/891.1 |
| 6,426,046 | B1 | * | 7/2002 | Cassells et al. | 422/99 |

FOREIGN PATENT DOCUMENTS

| | | | |
|---|---|---|---|
| DE | 4327845 | A1 | 3/1995 |
| DE | 100 30 474 | C1 | 2/2002 |
| EP | 0 011 144 | A1 | 5/1980 |
| WO | WO 96/03961 | | 2/1996 |
| WO | WO 9603961 | A1 | 2/1996 |
| WO | WO 96/23545 | | 8/1996 |
| WO | WO 03/105748 | A1 | 12/2003 |

* cited by examiner

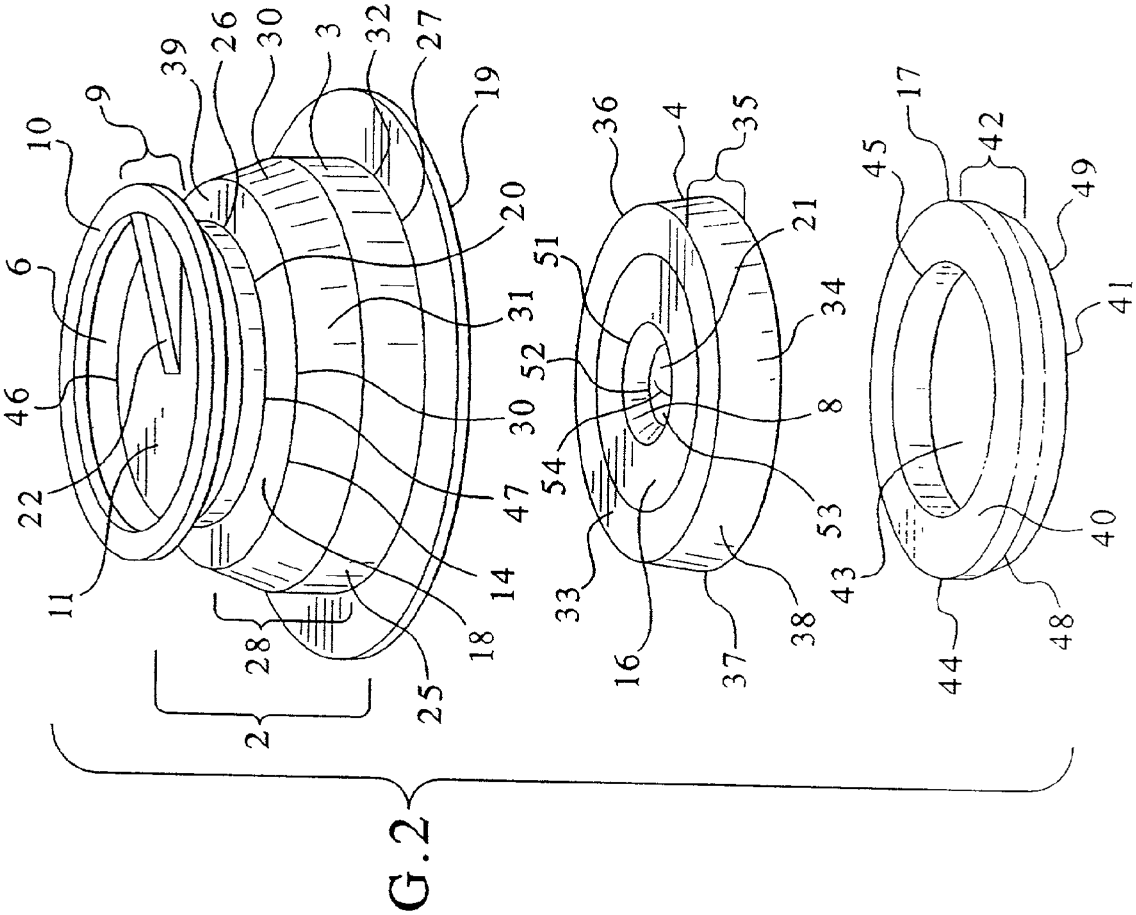
FIG. 2
FIG. 1
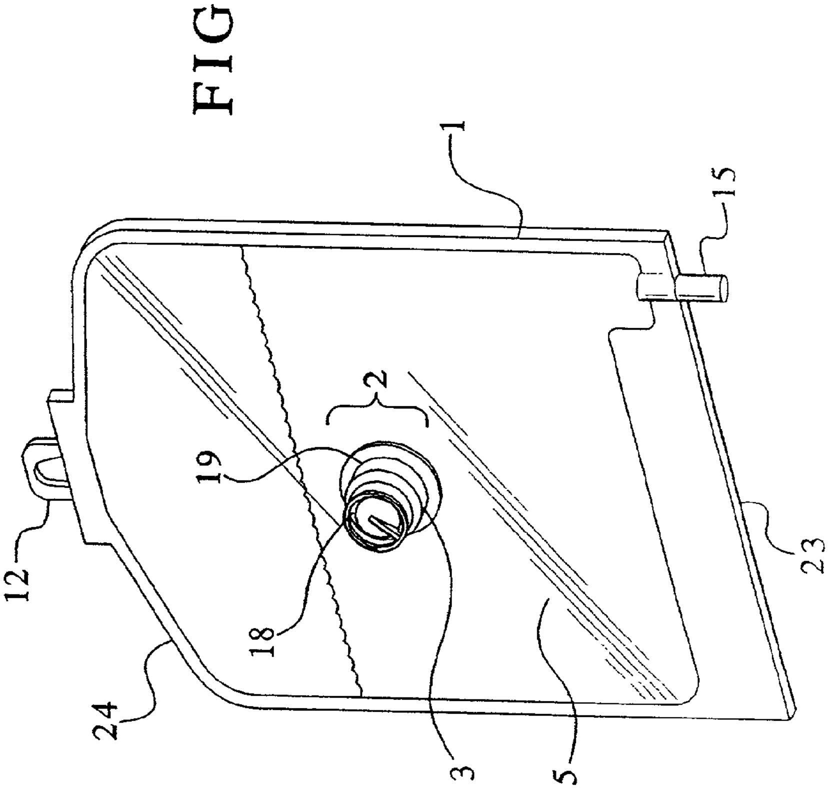

PORT, A CONTAINER AND A METHOD FOR ACCESSING A PORT

BACKGROUND OF THE INVENTION

The present invention generally relates to a medication port, an apparatus and a method for using a medication port for injecting or withdrawing a liquid from a container. More specifically, the present invention relates to a method for the injection or withdrawal of a liquid from a container via a medication port. Additionally, the present invention provides an apparatus and a method that may be used for the intravenous administration of a drug.

It is generally known that an individual may require a form of medication. Often, the medication must be administered to the patient intravenously. For example, it may be impractical or impossible to administer medication to the patient when the patient is unconscious. Additionally, administration of the medication to the patient orally may also be difficult in some cases. Further, the patient may require prolonged, constant and/or immediate medication which may only be administered intravenously. Of course, numerous other reasons exist for providing medication to a patient intravenously.

Liquids are often stored in containers constructed from, for example, flexible plastic or glass, and often contain a solution of saline, dextrose or lactated Ringer's, for example. An intravenous (IV) fluid drip generally connects an administration port located on the container with an artery in the patient. The mixed solution then flows from the administration port, through the IV, and to the bloodstream of the patient.

Further, it is generally known to provide a medication port to inject or withdraw a liquid from a container. For example, it is known to provide a medication port on the container through which a drug and/or other solutions may be administered. A needle or cannula is generally implemented to pierce a septum or membrane within the medication port of the container.

Known medication ports are often constructed as one-way valves which allow the addition of a medication to a container. However, known medication ports are often difficult to maintain in a sterile condition and, therefore, may be unsafe. Bacteria, viruses and/or other harmful substances, for example, dirt, may be present on the surface of the septum, membrane or container. As a result, such substances may be inadvertently introduced into the solution.

Typically, a medication port is constructed or attached to a container either as an up-port or as a side-port. The up-port is generally located at a distal end of the container while the side port is located on a sidewall of the container.

It is also generally known to provide a septum, also referred to as a bung, within an opening or port of the container. The septum prevents liquid inside of the container from leaving the container. Additionally, the septum reduces the risk of foreign substances from entering the container. Further, known septums often may be pierced by a needle or other object to establish fluid communication with the liquid in the container.

A cap is often incorporated with the port to enclose a septum. However, caps often completely surround the entire opening to the container. As a result, known caps are often bulky, expensive and inefficient. For instance, larger caps require more material in production and add weight and/or complexity to the entire apparatus.

A need, therefore, exists for a medication port as well as an apparatus and a method for injecting or withdrawing a liquid from a container to overcome deficiencies of known ports and apparatus and methods using such a port. Additionally, a need exists for a medication port which allows a liquid to be introduced to a container in a sterile environment.

SUMMARY OF THE INVENTION

The present invention provides a medication port, an apparatus and a method for using a medication port for injecting or withdrawing a liquid from a container. The container may include a solution to be administered to the patient. Additionally, the present invention provides for the injection or withdrawal of a liquid from a container via a medication port in an efficient and sterile manner. More specifically, the present invention may be used for the intravenous administration of a drug. The present invention also provides for a container with a medication port for injecting or withdrawing a liquid from a container.

To this end, in an embodiment of the present invention, an apparatus for injecting or withdrawing a liquid from a container is provided. The port has a housing having an interior defined by peripheral walls extending between a first end and a second end. The port has a septum within the interior at the first end of the housing. The port further has a cap on the first end of the peripheral walls of the housing wherein the cap encloses the first end of the housing and covers the septum. A line of separation is provided between the cap and the peripheral walls of the housing.

In an embodiment, the port has a lip extending between the peripheral walls and the cap at the first end of the housing.

In an embodiment, the port has a recess formed in the septum wherein the recess includes a slit.

In an embodiment, the port has a support ring in the interior of the housing wherein the support ring is between the septum and the second end of the housing.

In an embodiment, a ring is attached to the cap wherein the ring forms an opening between the ring and the cap.

In an embodiment, the septum has a tapered exterior wall that is secured in the interior of the housing.

In an embodiment, the cap has a diameter smaller than a diameter of the septum.

In an embodiment, the support ring has a diameter greater than a diameter of the septum.

In another embodiment, a container is provided having peripheral walls defining an interior wherein the interior holds a solution. The container has a port having walls defined between a first end and a second end attached to the wall of the housing having an interior. A septum is provided in the interior of the port. Further, a support ring is provided in the interior of the port wherein the septum is between the support ring and the first end of the port and a cap enclosing the first end of the housing wherein the cap covers the septum.

In another embodiment, the container has a line of separation between the cap and the first end of the housing.

In another embodiment, the container has a target area in the septum defined by a recess formed in the septum.

In still a further embodiment, the container has a slit in the septum.

In an embodiment, the container has a port integrally formed with the cap.

In an embodiment, the container has a ring extending from the first end of the container wherein the ring defines an opening.

In another embodiment of the present invention, a method is provided for accessing a container. The method has the steps of: attaching a port having walls defined between a first end and a second end wherein the second end is attached to the wall of the container and further wherein the port has a cap at the first end of the port; securing a septum within the housing; securing a support ring within the housing wherein the septum is between the support ring and the first end of the port; and removing the cap to expose only a portion of the septum.

In an embodiment, a needle is inserted through the septum.

In an embodiment, the cap is separated from the port at a line of separation.

In an embodiment, a ring is pulled having an opening attached to the cap to remove the cap from the port.

In an embodiment, a recess area is formed in the septum wherein the septum has a slit.

In an embodiment, the walls of the port have a length between the first end and the second end greater than a combined width of the septum and the support ring.

It is, therefore, an advantage of the present invention to provide a port, a container and a method for accessing a container for the injection or withdrawal of a liquid from a container.

Another advantage of the present invention is to provide a port, a container and a method for accessing a port using a medication port having a target area located under the cap.

Yet another advantage of the present invention is to provide a port, a container and a method for accessing a container which is compatible with a range of cannulas or needle gauges and lengths as well as with a range of insulin pens.

A still further advantage of the present invention is to provide a port, a container and a method for accessing a container which allows for the port to be located away from an administration port providing simplified accessibility to both ports and/or without interference from the other port.

Moreover, an advantage of the present invention is to provide a port, a container and a method for accessing a container for using a medication port which decreases risk of contamination.

And, an advantage of the present invention is to provide a port, a container and a method for accessing a container having a cap.

A still further advantage of the present invention is to provide a port, a container and a method for accessing a container having a rigid housing which reduces risk of cannula or needle sticking.

Additional features and advantages of the present invention are described in, and will be apparent from, the detailed description of the presently preferred embodiments and from the drawings.

BRIEF DESCRIPTION OF THE DRAWINGS

FIG. 1 illustrates a perspective view of a container with having a port in an embodiment of the present invention.

FIG. 2 illustrates an exploded isometric view of a port in an embodiment of the present invention.

DETAILED DESCRIPTION OF THE PRESENTLY PREFERRED EMBODIMENTS

Figure 3:
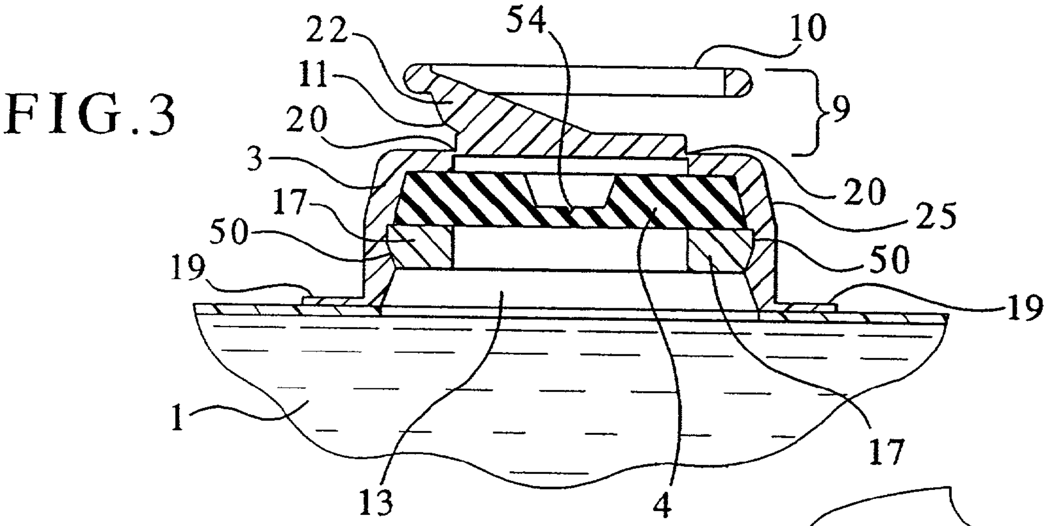
FIG. 3 illustrates a sectional view of a cap on the port in an embodiment of the present invention.

The present invention generally relates to a port, a container and a method for accessing a container for injecting or withdrawing a liquid from the container. Additionally, the present invention relates to a container having a port. More specifically, the present invention relates to a port, a container and a method for accessing a container to introduce a drug into the port.

Referring now to the drawings wherein like numerals refer to like parts, FIG. 1 generally illustrates a perspective view of a container 1 having a first end 23 and a second end 24. The container 1 may be peripherally sealed and may have a liquid 5 or other solution in an interior of the container 1. The container 1 may be constructed of a flexible material, such as a PVC or non-PVC material. Such containers are generally known and, as such, will not be described in further detail herein.

The container 1 may have a port 2 having a first end 18 and a second end 19. The medication port 2 of the present invention may be an up-port or a side port. In the embodiment shown in FIG. 1, the medication port 2 is a side-port. The container 1 is illustrated in a position as is common in actual use. More specifically, the container 1 may be positioned up-right and may have the medication port 2 elevated above an administration port 15 in actual use. Additionally, a strap 12 for, for example, a hook may be provided to hang the container 1 in, for example, an elevated position at or near a patient. When the container 1 is positioned at or near the patient, gravity may force the liquid 5 inside the container 1 through the administration port 15 to the patient. Preferably, the administration port 15 may be located remotely from the medication port 2 as illustrated in the embodiment shown in FIG. 1.

Referring now to FIG. 2, the port 2 may have a housing 3 which may have a wall 25. Preferably, the port 2 is a medication port through which a medicament may be added or a solution may be removed from the container 1. The housing 3 and the wall 25 may be constructed from, for example, rubber, plastic or any other material generally known to those skilled in the art. Additionally, the housing 3 may be constructed of rigid polypropylene which may reduce risk of a needle 7 puncturing the wall 25. Further, the housing 3 may be constructed using gamma-grade materials which are approved to withstand gamma irradiation prior to sterilization as a final stage of the manufacturing process. Gamma-grade materials allow for "pre-sterilization" and reduction in autoclaving exposure time.

As illustrated in FIG. 2, the wall 25 may be circular. The wall 25 of the housing 3 may have a first end 26 and a second end 27. The second end 27 of the wall 25 may be integrally formed with the second end 19 of the medication port 2. Additionally, the first end 26 of the wall 25 may be integrally formed with a cap 9 wherein the cap 9 may be separated from the first end 26 which will be described in further detail hereinafter.

The first end 26 of the wall 25 may also have a lip 39 which protrudes inward toward a center of the housing 3. The lip 39 may be in contact with a septum 4. The lip 39 may also secure the septum 4 within the housing 3 by friction, or, alternatively, the septum 4 may be sealed to the lip 39. The lip 39 of the wall 25 may have an inner circumference 47 and an outer circumference 14 as shown in FIG. 2.

The wall 25 may have a height 28 and may have a first circumference 30 at the first end 26 and a second circumference 32 at the second end 27. Additionally, the first circumference 30 at the first end 26 of the wall 25 may be smaller than the second circumference 32 at the second end 27 of the wall 25. The smaller circumference 30 at the first end 26 of the wall 25 may result in the wall 25 being tapered. More specifically, a taper 31 may result in the wall 25 tilting inward toward the center of the housing 3.

The septum 4 of the medication port 2 may be located within the wall 25 of the housing 3. Additionally, the septum 4 may be in contact with an inner wall 50 of the housing 3 as shown in FIG. 3. The septum 4 may be constructed from, for example, rubber, plastic or any other material generally known to those skilled in the art. Additionally, the septum 4 may be constructed of a polyisoprene material which may allow for the septum 4 to re-seal after puncturing the septum 4 by, for example, the needle 7.

As illustrated in FIG. 2, the septum 4 may be circular. The septum 4 may have a height 35 and may have a first circumference 36 and a second circumference 37. Additionally, the septum 4 may have a first end 33 and a second end 34. The first circumference 36 at the first end 33 of the septum 4 may be smaller than the second circumference 37 at the second end 34. The smaller circumference 36 at the first end 33 may result in the septum 4 being tapered. More specifically, a taper wall 38 may result as shown in FIG. 2 wherein an opening at a top side of the septum 4 is greater than at a center of the septum 4.

The first end 33 of the septum 4 may be in contact with the lip 39 of the wall 25. The lip 39 may secure the septum 4 in place within the housing 3 and may provide a liquid-tight fit between the septum 4 and the wall 25 of the housing 3.

The septum 4 may also have a target area 16 which may assist a health-care provider or other person with insertion of, for example, the needle 7 into the septum 4. Of course, a cannula or other object may be used to pierce-the septum 4. The target area 16 may also be colored, for example, red, to contrast with the color, for example, black, of the housing 3. Use of different colors may result in the target area 16 being more visible and/or distinguishable to the health-care provider or other person.

As further illustrated in FIG. 2, a recess 21 may be located within the target area 16 of the first end 33 of the septum 4. The recess 21 may assist the health-care provider or other person by providing a reduced resistance location to insert the needle 7 through the septum 4. The target area 16 may also have a slit 54 instead of, or in addition to, the recess 21.

The recess 21 may be formed by an internal wall 8 in the target area 16 of the septum 4. More specifically, the wall 8 may have a first circumference 51 at the first end 33 of the septum and a second circumference 52 at a valley 53 within the septum 4. The first circumference 51 at the first end 33 of the septum 4 may be greater than the second circumference 52 at the valley 53 in the septum 4. The difference in the circumferences of the internal wall 8 may result in the internal wall 8 being tapered.

The health-care provider or other person may puncture the septum 4 to establish fluid communication with the liquid 5 in the container 1. A support ring 17 may support the septum 4 when an object, for example, the needle, is pressed down upon the septum 4. As illustrated in FIG. 2, the support ring 17 may resemble, for example, a ring.

More specifically, when the health-care provider or other person inserts an object through the septum 4, pressure is created on the septum 4. The support ring 17 may allow pressure to be diverted from the outer periphery of the septum 4 onto the support ring 17. As a result, the septum 4 may be able to withstand a greater pressure with the support ring 17 than without the support ring 17. The support ring 17 may be constructed from, for example, rubber, plastic or any other material generally known to those skilled in the art.

The support ring 17 may be circular and may have a first outer circumference 44, a second outer circumference 49 and an inner circumference 45. Additionally, the support ring 17 may have a first end 40 and a second end 41. The first outer circumference 44 may be at the first end 40 and a second outer circumference 49 may be at the second end 41. The first outer circumference 44 may be greater than the second outer circumference 49. As a result, the support ring 17 may taper downward. More specifically, the support ring 17 may have a taper 48. The first outer circumference 44 and the second outer circumference 49 of the support ring 17 may be in contact with the inner wall 50 of the housing 3 as shown in FIG. 3.

The support ring 17 may also have a height 42 which may be smaller than the height 28 of the wall 25. The inner circumference 45 of the support ring 17 may form a hollow interior area 43 through which the needle 7 or other object may extend after piercing the septum 4.

The first end 40 of the support ring 17 may be in contact with the second end 34 of the septum 4. Additionally, the second end 41 of the support ring 17 may be in contact with a lip 13 on the container 1.

The housing 3 may also have a cap 9 that may be constructed from, for example, rubber, plastic or any other material generally known to those skilled in the art. The cap 9 of the housing 3 may have a cover 11 having a circumference 46. The cap 9 may also have a ring handle 10. As illustrated in FIG. 2, the cover 11 and the ring handle 10 may be circular. The ring handle 10 of the cap 9 may have a hollow opening 6 through which a user may insert, for example, a finger or hook.

The cover 11 of the cap 9 may also have a line of separation 20. The line of separation 20 may be a perforation, a score line or other line of weakness formed between the cover 11 and the lip 39 of the wall 25. The line of separation 20 may be formed at the circumference 46 of the cover 11. More specifically, the line of separation 20 may provide a circumferential point at which the cover 11 may be removed from a remainder of the housing 3.

The cover 11 may be integrally formed with the ring handle 10 by a connector 22 as generally shown in FIG. 2. The connector 22 may be secured to the cover 11 and the ring handle 10 so that a pulling force may break the line of separation 20.

FIG. 3 illustrates an embodiment of the medication port 2 of the present invention with the cap 9 secured to the wall 25 of the housing 3. More specifically, FIG. 3 illustrates the medication port 2 prior to removal of the cap 9.

When the cap 9 is on the housing 3, the cap 9 may protect the septum 4 and may create a sterile environment for the septum 4 by sealing the septum 4 from the surrounding environment. More specifically, when the cap 9 is secured to the wall 25 of the housing 3, dust, pathogens and other harmful substances may not access the septum 4 located within the housing 3.

Additionally, when the cap 9 is in the sealed position, the septum 4 may be protected from physical damage. The cap 9 may prevent accidental damage that may otherwise occur to the septum 4 if the septum 4 was unprotected.

Figure 4:
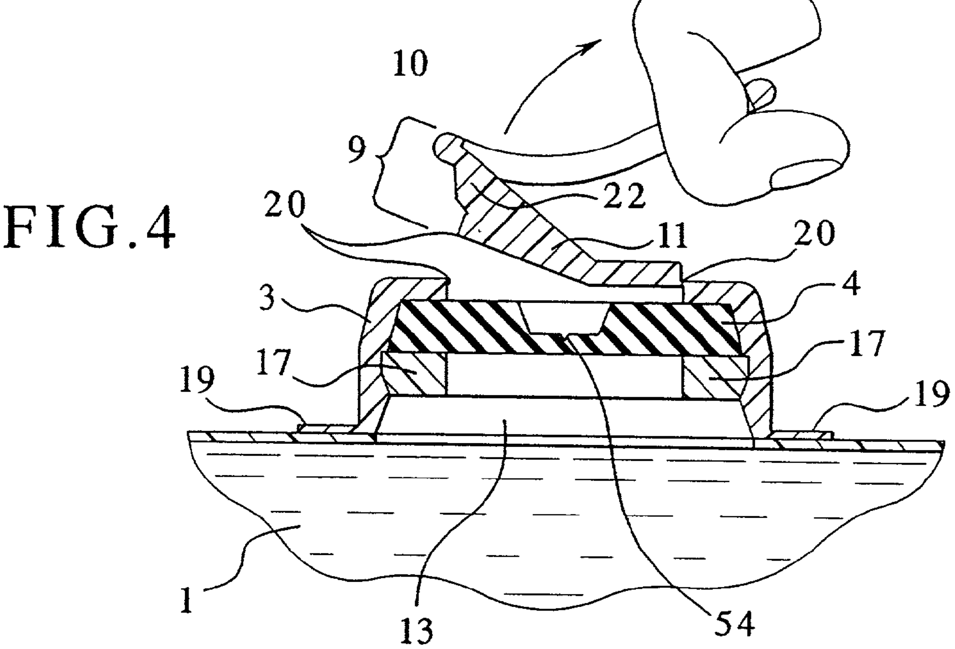
FIG. 4 illustrates a sectional view of a user removing a cap of the port in an embodiment of the present invention.

FIG. 4 illustrates an embodiment of the present invention with the cap 9 of the medication port partially removed. The ring handle 10 of the cap 9 may be lifted by, for example, a finger of a user or a hook. When the user pulls on the ring handle 10, the line of separation 20 may break and may allow the user to remove the cap 9. When the cap 9 is removed, the septum 4 may be exposed. Upon removal of the cap 9, the septum 4 may be ready for use through penetration of the septum 4 by, for example, the needle 7.

Figure 5:
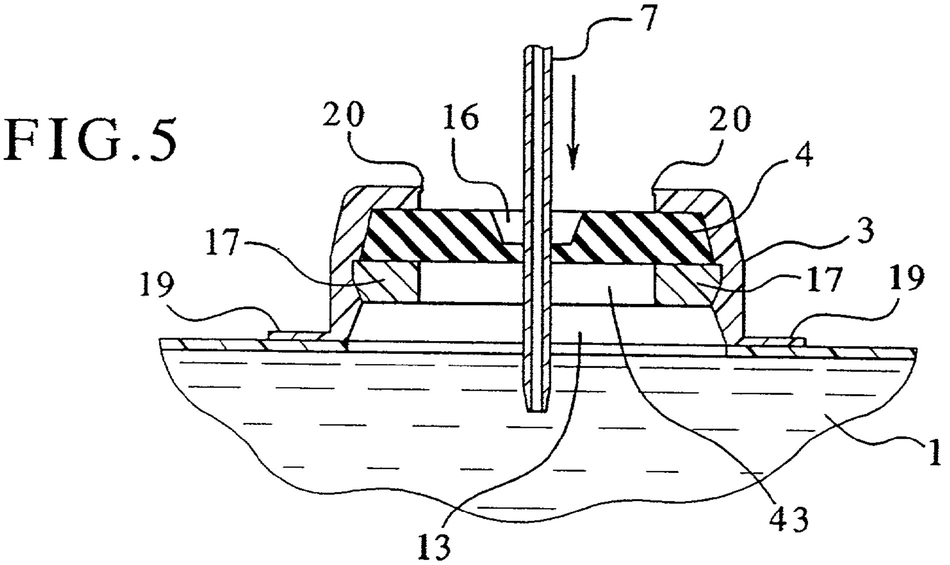
FIG. 5 illustrates a sectional view of a needle inserted into the port in an embodiment of the present invention.

FIG. 5 illustrates an embodiment of the medication port 2 of the present invention with the cap 9 removed from the wall 25 of the housing 3. FIG. 5 also illustrates the needle 7 inserted through the septum 4 to provide fluid communication with the liquid 5 inside the interior of the container 1.

The septum 4 may be punctured by the needle 7 or cannula (not shown). The needle 7 or other object may pierce the septum 4 through the target area 16 on the septum 4. The needle 7 or other object may then pass through the hollow interior 43 of the support ring 17. After the needle or other object is inserted into the container 1, liquid may be added or withdrawn to from the container 1 as may be required.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

We claim:

1. A port comprising:

a housing having an interior defined by peripheral walls extending between a first end and a second end;

a septum within the interior at the first end of the housing;

a cap on the first end of the peripheral walls of the housing wherein the cap encloses the first end of the housing and covers the septum;

a line of separation between the cap and the peripheral walls of the housing;

a lip extending between the peripheral walls and the cap at the first end of the housing; and a support ring in the interior of the housing wherein the support ring is between the septum and the second end of the housing.

2. The port of claim 1 further comprising:

a recess formed in the septum wherein the recess includes a slit.

3. The port of claim 1 further comprising:

a ring attached to the cap wherein the ring forms an opening between the ring and the cap.

4. The port of claim 1 wherein the septum has a tapered exterior wall that is secured in the interior of the housing.

5. The port of claim 1 wherein the cap has a diameter smaller than a diameter of the septum.

6. The port of claim 1 wherein the support ring has a diameter greater than a diameter of the septum.

7. A container comprising:

peripheral walls defining an interior wherein the interior holds a solution;

a port having walls defining a housing, the housing having first and second ends and an interior therebetween wherein the port is attached to one of the peripheral walls;

a septum in the interior of the housing;

a support ring in the interior of the housing wherein the septum is between the support ring and the first end of the port;

a cap enclosing the first end of the housing wherein the cap covers the septum; and a lip extending between the walls of the port and the cap at the first end.

8. The container of claim 7 further comprising:

a line of separation between the cap and the first end of the housing.

9. The container of claim 7 further comprising:

a target area in the septum defined by a recess formed in the septum.

10. The container of claim 7 further comprising:

a slit in the septum.

11. The container of claim 7 wherein the port is integrally formed with the cap.

12. The container of claim 7 further comprising:

a ring extending from the first end of the container wherein the ring defines an opening.

13. A method for accessing a container wherein the container has walls defining an interior, the method comprising the steps of:

attaching a port having walls defined between a first end and a second end and defining a housing, wherein the second end of the port is attached to one of the walls of the container and further wherein the port has a cap at the first end of the port, and wherein the port has a lip that extends between the walls of the port and the cap at the first end;

securing a septum within the housing;

securing a support ring within the housing wherein the septum is between the support ring and the first end of the port;

removing the cap to expose only a portion of the septum.

14. The method of claim 13 further comprising the step of:

inserting a needle through the septum.

15. The method of claim 13 further comprising the step of:

separating the cap from the port at a line of separation.

16. The method of claim 13 further comprising the step of:

pulling a ring having an opening attached to the cap to remove the cap from the port.

17. The method of claim 13 further comprising the step of:

forming a recessed area in the septum wherein the septum has a slit.

18. The method of claim 13 wherein the walls of the port have a length between the first end and the second end greater than a combined width of the septum and the support ring.

* * * * *